United States Patent
Leen

(10) Patent No.: US 8,826,519 B2
(45) Date of Patent: Sep. 9, 2014

(54) SYSTEM FOR REPLACING THE WATER COOLED LASER IN A MICROPLATE READER

(71) Applicant: Thomas Leen, Raleigh, NC (US)

(72) Inventor: Thomas Leen, Raleigh, NC (US)

(*) Notice: Subject to any disclaimer, the term of this patent is extended or adjusted under 35 U.S.C. 154(b) by 0 days.

(21) Appl. No.: 13/871,451

(22) Filed: Apr. 26, 2013

(65) Prior Publication Data
US 2013/0232771 A1 Sep. 12, 2013

Related U.S. Application Data

(62) Division of application No. 12/693,128, filed on Jan. 25, 2010, now Pat. No. 8,448,322.

(60) Provisional application No. 61/147,080, filed on Jan. 24, 2009.

(51) Int. Cl.
B23P 19/00 (2006.01)
G01N 21/64 (2006.01)
G01N 21/17 (2006.01)

(52) U.S. Cl.
CPC .............. *G01N 21/17* (2013.01); *G01N 21/645* (2013.01)
USPC ........... 29/729; 29/402.01; 29/592.1; 29/700; 356/317; 356/318; 356/417; 356/440; 356/931

(58) Field of Classification Search
USPC ............ 29/402.01, 700, 729, 592.1; 356/317, 356/318, 417, 440, 931, 928
See application file for complete search history.

(56) References Cited

U.S. PATENT DOCUMENTS

| | | | | |
|---|---|---|---|---|
| 5,151,909 A * | 9/1992 | Davenport et al. | ............. | 372/22 |
| 5,355,215 A | 10/1994 | Schroeder et al. | | |
| 6,985,225 B2 * | 1/2006 | Bechem et al. | ............... | 356/317 |
| 7,170,597 B1 * | 1/2007 | Hooper et al. | ................ | 356/317 |
| 7,265,829 B2 * | 9/2007 | Jiang et al. | ..................... | 356/328 |
| 7,408,637 B2 * | 8/2008 | Freeling et al. | ............... | 356/317 |
| 7,700,928 B2 * | 4/2010 | Rasnow et al. | ............ | 250/458.1 |
| 7,994,485 B2 * | 8/2011 | Feke et al. | ................. | 250/458.1 |
| 8,218,141 B2 * | 7/2012 | Zimenkov et al. | ............ | 356/319 |
| 8,305,580 B2 * | 11/2012 | Aasmul | ......................... | 356/417 |
| 8,347,478 B2 * | 1/2013 | Leen | ......................... | 29/402.01 |
| 8,448,322 B2 * | 5/2013 | Leen | ......................... | 29/402.01 |
| 2003/0010930 A1 * | 1/2003 | Thorwirth | .................. | 250/458.1 |
| 2005/0190366 A1 * | 9/2005 | Boege et al. | .................. | 356/417 |

* cited by examiner

*Primary Examiner* — Peter DungBa Vo
*Assistant Examiner* — Azm Parvez
(74) *Attorney, Agent, or Firm* — James G. Passe; Passe Intellectual Property, LLC

(57) ABSTRACT

The present invention relates to a method and system for repairing and refurbishing a microplate reader of the Flipr type which has a water cooled argon laser light source. The old laser is removed and replaced with a high power (300 to 500 mW) air cooled solid state laser as a replacement place on its own support and focused and wired to replace the old laser. The new product operates at lower power consumption yet provides accurate measurements.

4 Claims, 2 Drawing Sheets

SYSTEM FOR REPLACING THE WATER COOLED LASER IN A MICROPLATE READER

This application is a Divisional of U.S. non-provisional application Ser. No. 12/693,128 filed on Jan. 25, 2010, now U.S. Pat. No. 8,448,322 issued on May 28, 2013, which is hereby incorporated by reference. This application also claims the benefit of U.S. provisional application 61/147,080 filed on Jan. 24, 2009 and is included herein in its entirety by reference.

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

1. Field of the Invention

The present invention relates to a method and system for replacing a lighting system in an existing microplate reader with a new light source. Specifically, the present invention relates to a system which can be used to replace a water cooled laser with an LED light system in an existing microplate reader.

2. Description of Related Art

The use of fluorescence analytical monitoring techniques is well known. Fluorescence measurements can be taken by shining a light source of a first wavelength and then when the sample of light is absorbed, the test material is induced to emit light of a second wavelength. Measurement of the second wavelength light, either as length, intensity or the like, can be used to correlate the activity in a cell that is producing the secondary fluorescence. Physiological parameters can then be determined based on the results, such as potassium or other ion channel activity. Florescence type measurements are of great importance to the research and development of new pharmaceutical compositions and are used to screen a variety of tissues for interaction with most any chemical composition that is of interest in affecting the measurable systems.

Typically, in the analysis of cells, a variety of older machines are available for using this type of technique with 96 or 384 well multiple well plates. These machines provide a multiwall plate holder, a water cooled laser light source and some form of a receiving camera for detecting the cell's second wavelength light emissions. The cells are cultured in each of the wells at the bottom with a growth medium provided over the growing cells. The chemical compound to be tested or otherwise assayed is played into the liquid in each well with the florescent material and the effect measured by excitation by the laser and reading by the camera. For example, in U.S. Pat. No. 5,355,215 to Schroder et al issued Oct. 11, 1994, there is disclosed a method for aligning a camera and a light source for measuring the second wavelength with a minimum about if interference from the supernate liquid. This process has been utilized extensively and appears in later machines and in more recently issued patents, for example, in U.S. Pat. No. 7,265,829 issued Sep. 4, 2007 to Jiang et al.

The older microplate reader machines that utilize water cooled lasers, while difficult to use, were well built and very cost effective. Such machines include the Flipr2® and Flipr3® microplate readers. These machines suffered from the difficulty of using and operating water cooled lasers but because parts were relatively accessible for repair, a burgeoning business in repair and refurbishment developed to keep these machines in service. Since the refurbishment of even a patented product is allowable repair, such repair has been accomplished not only by OEMs, but a variety of small companies also repair these types of machines. The lasers in these machines are typically in the 3 watt water cooled argon laser with power designed to be sufficient in order to provide sufficient light to produce excitation of each well in a microplate.

Newer microplate reader machines are very costly and tend to be large in an attempt to avoid the difficulties in using water cooled lasers. An example is the Flipr$^{tetra}$® made by the same company as the older Flipr2 and Flipr3 machines, Molecular Devices (MDC). In order to encourage purchases of newer models of microplate readers, MDC has declined to support its older machines and encourage users of the older machines to upgrade. However, for many users the older machines are fine and there is a desire in the marketplace to continue refurbishing these machines. The fact that water cooled lasers that these machine were built to utilize are expensive, hard to use and getting scarce to fit the existing machines, has suggested the repair life of these machines is limited in spite of the desire of users to continue using the machines to the end of their useful life.

Digital lasers are now well known and can be obtained in a variety of wattages. However, the wattages of the air cooled laser types has not yet reached the 3 watts that are currently employed and rated for the existing machines with water cooled lasers. In fact, currently the largest air cooled lasers are in the 500 mW range and industrially considered not powerful enough to be used in a microplate reader.

BRIEF SUMMARY OF THE INVENTION

The use of argon water cooled lasers has been extensively used by microplate readers. These lasers are sensitive and easily misaligned. The microplate readers used with them were designed, shaped and calibrated specifically to be used with these types of lights sources. It has been discovered that it is possible to replace the light source with 300 to 500 mW air cooled laser light source under specific conditions and repair such a unit and use filters holders supports, and the like, of the present invention thus extending the useful repair life of these older microplate readers without the problems normally associated with argon water cooled lasers and surprisingly with a laser one-sixth the power of OEM lasers in microplate readers with water cooled lasers.

In one embodiment of the present invention, there is a method for repairing a fluorescence microplate reader having a water cooled laser light source of about 3 watts that has been removed from the reader comprising:
  a) selecting an air cooled laser having a wattage of between about 300 and 500 mW, having a total lumen output sufficient to produce a replacement lumen output, the air cooled laser mounted in a rigid support and provide light to the microplate reader;
  b) providing that the light output of the air cooled laser is at a desired wavelength;
  c) positioning the support such that the light from the air cooled laser shines on the bottom of a microplate positioned in the reader; and
  d) connecting the air cooled laser to the reader such that they operate in place of the water cooled laser light.

In another embodiment of the invention, there is a system for replacing a water cooled laser in a fluorescence microplate reader comprising:

a) An air cooled laser having a power of about 300 to 500 mW mounted in fixed relationship having a lumen output sufficient to produce a replacement lumen output;

b) an optional filter for changing the wavelength of the LED lights to a desired wavelength where the wavelength of the air cooled laser is not originally a desired wavelength;

c) a support for adjustably positioning the air cooled laser and optionally the filter in the reader such that when placed in the reader the light from the air cooled laser shine on the bottom of a microplate placed in the reader.

DETAILED DESCRIPTION OF THE INVENTION

Figure 1:
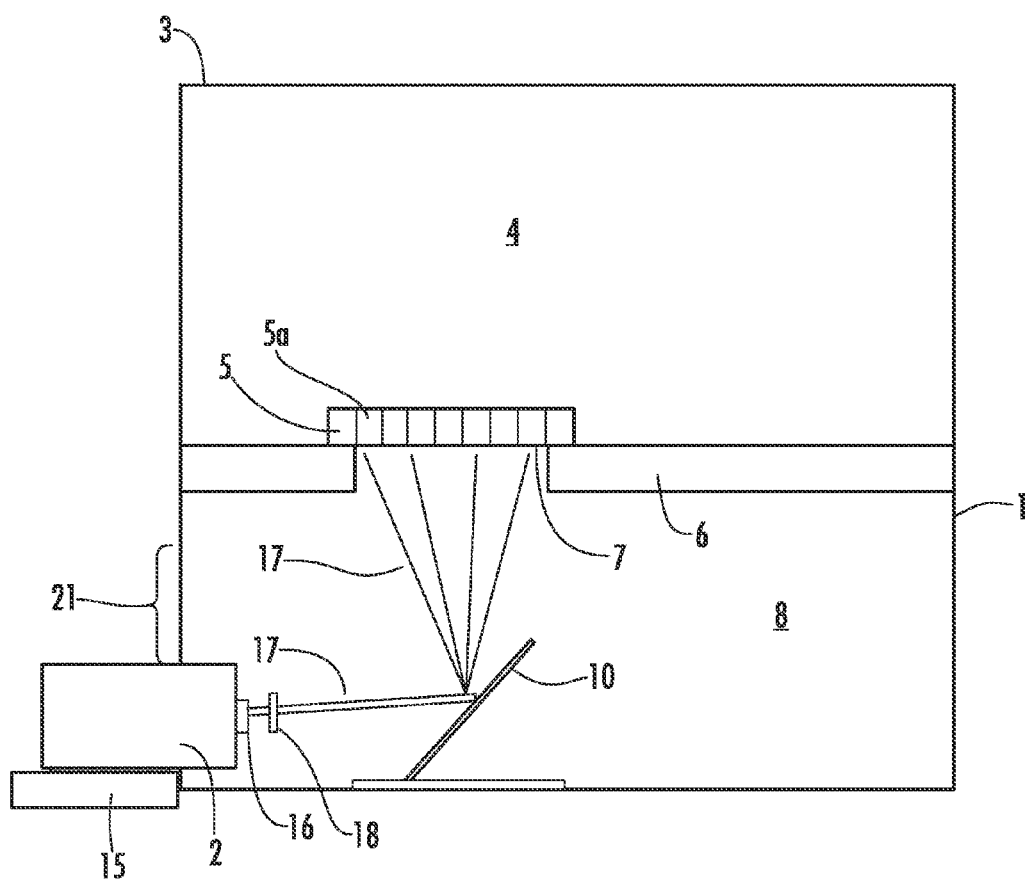
FIG. 1 is a side view of a microplate reader with an air cooled laser light source positioned partially outside the reader.

While this invention is susceptible to embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings. This detailed description defines the meaning of the terms used herein and specifically describes embodiments in order for those skilled in the art to practice the invention.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein, is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are for the purpose of illustrating certain convenient embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As used herein a "fluorescence microplate reader" refers to those microplate readers which originally were designed to handle 384 plate readers or less and use a water cooled laser such as an argon water cooled laser to provide an excitation light source. Argon lasers provide a light of a wavelength of about 488 nanometers. Units such as the FLIPR2 and FLIPR3 unit made by MDC are examples of the intended microplate readers that are repaired using the method and system of the present invention. While the argon lasers do work for their intended purpose in these types of microplate readers, they are difficult to use, have a long warm up time and need to be frequently adjusted. When replacing the lasers during the repair or refurbishment process, it is understood that the laser would be removed before beginning with the method and system of the present invention. These types of microplate readers have an upper portion where pipetting is done to a microplate sitting or placed in the reader. Once a microplate is placed in the reader the bottom surface of the microplate is exposed to the bottom portion of the reader where a light source, such as the argon laser, can shine on the bottom surface of the plate specifically so that it shines on each well bottom surface. Light emissions from the microplate wells occurs in the lower position as well and reaches a CCD type camera either directly or indirectly by any of one or more mirrors.

As used herein, "air cooled laser" refers to digital air cooled lasers. These are also referred to as optically pumped semiconductor lasers. These are the highest power air cooled solid state lasers currently commercially available. They are available in wattages of about 500 mW and below and have a wavelength light of 488 nm. These are considered high power lasers of these types even though much higher power lasers are available in the argon water cooled typed which came stock in the type of microplate readers being repaired by the method of this invention. These are typically a blue light laser and certainly could have a range of blue light from about 425 to about 510 nm. One example of such a unit is the Sapphire 488-500 Laser head produced as a 500 mW CW blue laser having an output of 488 nm by Coherent. It is known in the art that these type of lasers work with their own controller and frequently an appropriate heat-sink instead of the water cooled versions of lasers. One skilled in the art in view of this disclosure could adapt the air cooled laser accordingly. While the unit being replaced has a very high power 3 watt laser. It has been surprisingly found that replacing the water cooled laser with an air cooled high power laser of from about 300 mW up to the maximum 500 mW actually surprisingly still works as a light source for a microplate reader when replacing it from the standard water cooled laser.

It has also been discovered that a more homogeneous lighting can be achieved by filtering the light or passing the light from the air cooled laser through a filter or aperture of some kind. These embodiments provide a more even lighting on the bottom of a microplate during reading, and thus when tested, results in a coefficient of variation (CV) of 0.6% or about the same as a water cooled laser. One skilled in the art and understanding the problems described herein can vary the choice of air cooled lasers and filters or apertures to optimize the light source in view of the disclosure herein.

The air cooled laser needs to be held in relative fixed relationship so that light emanating from the air cooled laser remains constant within the beam produced. The stand or mounting bracket, or the like, can keep the relative position of the air cooled laser constant but must be able to be adjusted when in place in order to focus the air cooled laser relative to a microplate bottom that the air cooled laser is shining on. By mounting the holder on a support the air cooled laser can be adjusted in three dimensional space relative to the microplate bottom surface. One can easily fashion such adjustment means within the scope of the invention based on the disclosure herein and such is well within the skill in the art. The air cooled laser can be fixedly attached to such support or they can be set by gravity or other means on the support as desired. The fixed method of attaching to a support does allow the support and air cooled laser to be placed as a unit within the reader and thus makes replacement and set up much quicker and simpler.

In one embodiment, the air cooled laser is further contained within a case such as a box or the like. Such case would have a single opening in a single direction. Thus, stray light for the air cooled laser would be minimized and result in less overall light "noise" in reading the results of experiments with the air cooled laser based reader. Since scattered light has been discovered to be a potential problem with the present invention, where such is a problem additional dark, black or the like material can be positioned around the inside of the reader as desired to reduce the bounce light effect from the air cooled laser of the invention.

In order to change the light wavelength to the wavelength the reader needs, or more particularly the cells within a microplate need, to fluoresce. One may need to position a light filter which changes the wavelength of the air cooled laser emissions to the desired wavelength. Where one is attempting to duplicate the argon water cooled laser a filter which will cause the wavelength to change to 488 nanometers would be used unless as the example proposed the laser is already at the same wavelength. Typical pass filters are in the 480 to 550 nanometer range but can easily be chosen by one skilled in the art based on the selection of the air cooled laser and the desired end wavelength in view of this disclosure. Other wavelengths as desired could be obtained with appropriate filters. Such filters are available in the art. The luminosity is always decreased when passing through a filter and such must be considered and the luminosity matched to the particular filter since each filter may filter out more or less of the luminosity of the original air cooled laser lights. The size of the filter is sufficient to allow the air cooled laser light to pass entirely through the filter. Restricting the size of the filter can be used to focus and homogenize the emitted light as desired and the size of the desired filter and the distance from the air cooled laser while critical to the practice of the invention can be determined with minimum experimentation by one skilled in the art in view of this disclosure. One embodiment has the filter attached to the air cooled laser case or in another embodiment attached to or supported by the support that supports the air cooled laser lights.

The air cooled laser light must when replacing the water cooled laser, shine such that the filtered or unfiltered light shines on the bottom surface of a microplate placed in the reader. This can be done from an angle (less than 90 degrees) as taught by the art cited above or in other embodiments shining at 90 degrees directly or by way of a bounce mirror. The bounce mirror, in some embodiments, can be a dichroic mirror which allows the air cooled laser light to bounce off the dichroic mirror and hit the bottom surface of the microplate reader. Then when the emitted light comes from the bottom surface of the microplate, it can pass down through the dichroic mirror to a receiver below the mirror as long as the angles are correct for use of such a mirror. In one embodiment, a dichroic mirror that bounces light at 45 degrees is used. Air cooled laser light hits the mirror at 45 degrees and is reflected to the bottom surface of a microplate in the reader. The emitted light from the microplate exits at 90 degrees passes through the dichroic mirror and to the CCD camera in the reader positioned below the dichroic mirror. This can be seen as discussed with the figures which follow.

The support for the air cooled laser and optionally the filter or dichroic mirror serves at least two purposes. First, it keeps the parts in relative position to one another and makes 3 dimensional adjustments easier without changing their relative positions. Second, the support allows the system to be placed in an individual reader in such a way that it is immediately positioned for use by positioning the support in the predetermined position for replacing the original water cooled mirror. This forgoes the problems of finding the optimum position for each component and then doing the final 3D micro adjustments necessary to align and focus the light. The complete support can be placed into the reader and attached thereto and the installation is essentially complete with only final adjustment calibrations necessary. This embodiment, either with or without the dichroic filter embodiment, allows for quick easy repair, easy adjustment and a lower cost to repair than either replacing the laser or starting with each individual component.

Lastly, it has been discovered that this system can be turned on and off as the laser was using essentially the same means within the reader. Such is surprising since the units were not designed to accept anything other than water cooled argon laser light sources. The software if necessary can be modified as well but one skilled in the art can easily program the unit consistant with the repair/replacement of the water cooled unit.

Now referring to the drawings, FIG. 1 is a side view of a method and air cooled laser system 1 of the present invention showing an air cooled laser 2. The air cooled laser 2 is positioned partly outside the microplate reader 3. In this example is shown the inside front view of microplate reader 3. The upper interior 4 of the reader is where a microplate 5 in which are positioned a number of wells 5a. Microplate 5 sits or rests on microplate support 6 and exposes the bottom surface 7 of microplate 5 to lower interior 8. The laser light from the original water cooled laser in the original microplate reader shines on the bottom 7 and the excitation light from wells 5a shines down from the microplate 5 and is captured by a camera not shown in this view. In this view a bounce mirror 10 is shown. The system 1 of the present invention consists of the air cooled laser 2 which is placed and attached to support 15 and optional holders to fix the laser 2 in place and aid with adjustment and focusing. The support 15 gives the air cooled laser 2 the correct height and position subject to final micro adjustments and allows the air cooled laser 2 to be placed as a unit without need for total customization for each unit. The laser 2 could also be positioned within a box, not shown, in order to reduce stray light and further focus the light. Such box could be opaque and a dark or black color can be used to further aid in preventing stray light. If a filter is necessary, it can be placed in front of the laser opening 16 where laser beam 17 exits from the laser 2. A filter holder or aperture device can be attached to a box the reader 3 or mounted in any convenient manner if present and could easily be accomplished in view of the disclosure herein. Note the holders and supports can be provided with means to adjust in 6 degrees of freedom the actual aiming of the laser 2 to focus on the bottom 7 of the microplate 5.

One tremendous advantage of the present system 1 is that the entire unit can easily replace the laser of the unit by placement of the system in the open compartment of the lower chamber 8 or as shown in the microplate reader 3 as a single unit. It has been discovered that when the air cooled laser 2 is connected via wire 21 to the controls (not shown) of microplate reader 3, that a light system which does not have all the frailty of the previous water cooled laser light source is created in a device originally designed for use only with a water cooled argon laser (3W). It is also determined that such can be accomplished without the need to rebuild the reader 3 and mere refurbishment is possible. One will note that the original mirror 10 can remain in place and as such the camera which reads fluorescence from the microplate 5 does not need to be adjusted or removed. Within the space given one can fit the system 1 of the unit in place and either have the components pre-adjusted or individually adjust the laser 2 position and optional filter position relative to one another. By providing a support 15, it is possible to eliminate the need to constantly adjust the height of the system 1 relative to the bottom 7.

Figure 2:
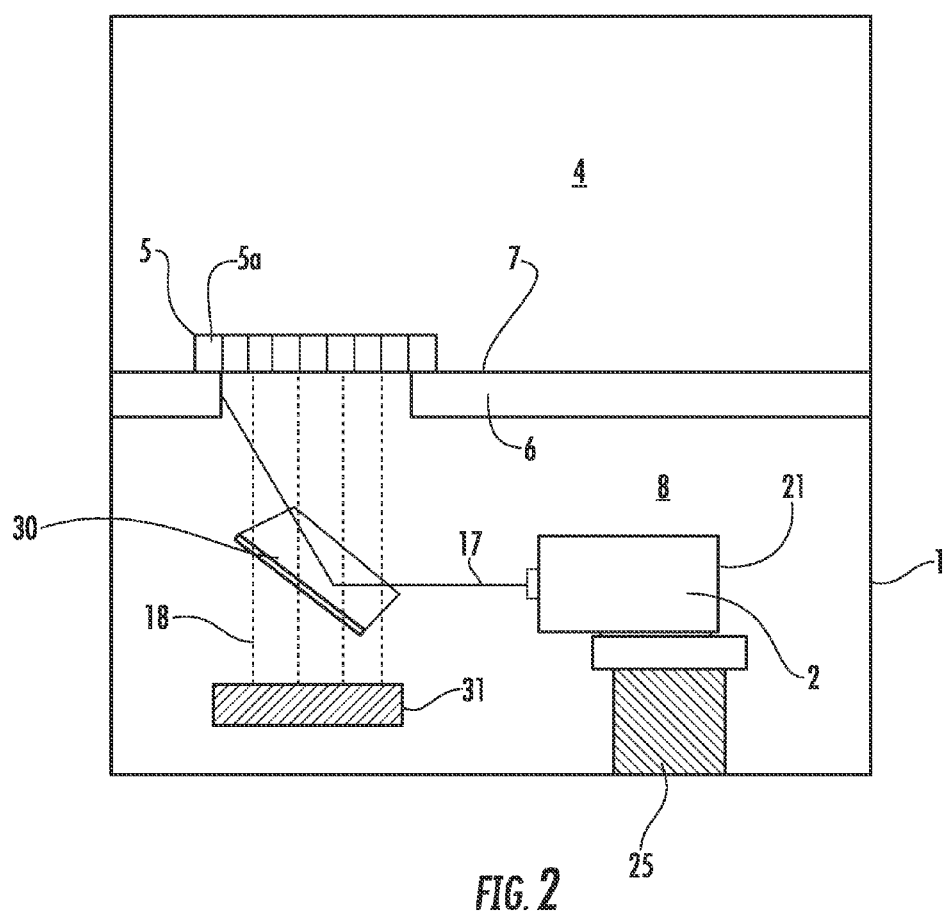
FIG. 2 is a side view of a microplate reader with an air cooled laser light source positioned inside the reader and using a dichroic mirror.

FIG. 2 involves a separate embodiment of the present invention where it is desirous to shine the laser 2 light at 90 degrees and where the mirror would otherwise be in the way of the CCD camera. In this embodiment, the system 1 consists of support 25 which supports the air cooled laser 2 and allows the entire system to be positioned inside the reader 3 in the lower interior 8. In order to utilize a 90 degree light in this embodiment, a dichroic mirror 30 is used. The dichroic mirror 30 is positioned at a 45 degree angle or as needed for the particular installation. Light shining from the laser 2 shines through an optional filter not shown and hits mirror 30 reflecting up and hitting bottom 7 at 90 degrees. The emissions 18 generated in the wells 5a shines downward at 90 degrees but passes directly through the dichroic filter 30 and can hit original reflective mirror 10 (not shown in this figure) or picked up by CCD camera 31. This arrangement has the advantage of once again positioning the system in the lower interior 8 a direct beam and not a 45 degree angled beam. Non-reflective material can also be added to interior 8 if reflectance becomes a problem with a particular repair.

Air cooled laser replacement using the method and system of the present invention will add longevity to the FLIPR readers and has been discovered to increase the time between light related refurbishment since when using the system of the present invention refurbishment times between work increases dramatically. In addition, a much lower power consumption can be used with the air cooled lasers, thus, saving energy which could eventually lead to a cost saving that pays for a replacement even when the water cooled laser does not need replacement. Accordingly, the results achieved with the present invention not only provide a quick and easy way to refurbish a FLIPR machine they surprisingly add longevity to the readers and provide a result not anticipated with air cooled laser use in a refurbishment situation.

Nothing in the embodiments is designed to be limiting unless otherwise stated. In view of the disclosure of the embodiments once can easily see if skilled in the art other substitutions of filters, support materials, air cooled lasers, and the like within the scope of the present invention. The claims which follow should not therefore be read as so limiting.

What is claimed is:

1. A system for replacing a water cooled laser in a fluorescence microplate reader comprising:
   a) an air cooled laser having a power of about 300 mW or more mounted in fixed relationship having a lumen output producing a replacement lumen output;
   b) a support for adjustably positioning the air cooled laser such that when placed in the reader the light from the air cooled laser shine on the bottom of a microplate placed in the reader.

2. A system according to claim 1 which further comprises a dichroic mirror for reflecting the filtered light from the system to the bottom of the microplate.

3. A system according to claim 1 which further comprises a filter for changing the wavelength of a LED light in the system to a different wavelength where the wavelength of the air cooled laser is not the original wavelength.

4. A system according to claim 3 which further comprises a support for adjustably positioning the filter.

* * * * *